United States Patent [19]

Childs et al.

[11] 4,334,539
[45] Jun. 15, 1982

[54] ELECTROSURGICAL GENERATOR CONTROL APPARATUS

[75] Inventors: Warren L. Childs, Blanchard; William T. Cronenwett, Norman, both of Okla.

[73] Assignee: Cimarron Instruments, Inc., Oklahoma City, Okla.

[21] Appl. No.: 144,363

[22] Filed: Apr. 28, 1980

[51] Int. Cl.$^3$ .............................................. A61B 17/36
[52] U.S. Cl. ........................... 128/303.14; 128/303.17; 307/117
[58] Field of Search ...................... 128/303.13, 303.14, 128/303.17; 307/117

[56] References Cited

U.S. PATENT DOCUMENTS

3,699,967 10/1972 Anderson ........................ 128/303.14
3,801,800 4/1974 Newton ....................... 128/303.14 X
3,897,788 8/1975 Newton ........................... 128/303.14
4,071,028 1/1978 Perkins ........................... 128/303.14
4,123,673 10/1978 Gonser ........................... 128/303.14

Primary Examiner—Lee S. Cohen
Attorney, Agent, or Firm—E. Harrison Gilbert, III

[57] ABSTRACT

A control unit for use with a hand-held probe and an electrosurgical generator is disclosed to include a power input transformer which isolates the primary power supply from two electrically isolated circuits within the control unit. A first one of the electrical circuits receives a channel select signal from a hand-held probe connected thereto and, in response thereto, actuates either a first channel circuit or a second channel circuit within the second circuit. Each of the first and second channel circuits includes an alternating current actuated relay for electromagnetically moving a switch element therein in response to the channel select circuit so that either a first or a second control signal is provided to the electrosurgical generator.

21 Claims, 4 Drawing Figures

ELECTROSURGICAL GENERATOR CONTROL APPARATUS

BACKGROUND OF THE INVENTION

1. Field of the Invention

This invention relates generally to electrosurgical generator apparatus and more particularly, but not by way of limitation, to apparatus for controlling an alternating current signal generator so that either a first alternating current signal or a second alternating current signal is provided to a workpiece engaging means, such as a hand-held probe.

2. Description of the Prior Art

In the medical field of surgery it is known that electric current can be used in the surgical cutting and coagulation of tissue. For example, a sinusoidal radio frequency current signal may be used to cleanly cut tissue, whereas an intermittant, exponentially decaying sinusoidal radio frequency current signal can be used to quickly destroy tissue. Such electric currents can be applied to the tissue through a probe under control of either a foot-controlled switch or a finger-controlled switch. An example of an electrosurgical generator apparatus which is operated via a finger-actuated switch mounted in a hand-held probe is disclosed in U.S. Pat. No. 4,071,028 in the name of Perkins. Another example of a finger-actuated control unit for an electrosurgical generator is an apparatus manufactured under the name Aspen Labs.

Although the surgical use of electric current is well known and devices which use electric current to surgically cut and/or coagulate tissue have been proposed or manufactured, these devices fail to separately isolate a primary power supply from each of two electrically isolated circuits within the control unit of the electrosurgical generator apparatus; and they do not isolate, through alternating current actuated relays, control signals which are provided to an alternating current signal generator means from circuits of the control unit while also providing dual mode control signals from a single hand-held probe to select either of two surgically usable alternating current signals.

SUMMARY OF THE INVENTION

The present invention overcomes the above-noted and other shortcomings of the prior art by providing a novel and improved electrosurgical generator control unit apparatus. This apparatus includes means for separately isolating a primary power supply from each of two electrically isolated circuits which are also included within the control unit. Furthermore, the present invention includes means for isolating control signals for actuating an alternating current signal generator from the circuits of the control unit by using alternating current actuated relays. The present invention further provides means by which either of two control signals can be provided to the alternating current signal generator under control of a single hand-held probe.

Broadly, the present invention provides an apparatus for controlling an electronic surgical instrument which includes an alternating current signal generator means and a workpiece engaging means. This apparatus includes a first channel circuit means for providing a first control signal to the alternating current signal generator means and second channel circuit means for providing a second control signal to the alternating current signal generator means. The apparatus constructed in accordance with the present invention further includes channel select means for selectively actuating either the first channel circuit means or the second channel circuit means so that when the first channel circuit means is actuated, the first control signal is provided to the alternating current signal generator to activate the generation thereby of a first alternating current signal surgically usable by the workpiece engaging means and so that when the second channel circuit means is actuated, the second control signal is provided to the alternating current signal generator means to activate the generation thereby of a second alternating current signal surgically usable by the workpiece engaging means. The apparatus of the present invention further includes power input means comprising a first electrical winding having an input means for connecting the first electrical winding to a source of alternating current, a second electrical winding associated with the channel select means, a third electrical winding associated with the first channel circuit means and the second channel circuit means, and core means for inductively coupling the first electrical winding with the second and third electrical windings.

The first channel circuit means includes first electronic switch means, responsive to the channel select means, for switchably connecting the first control signal to the alternating current signal generator means and first channel circuit isolator means for electrically isolating the channel select means from the first electronic switch means. The second channel circuit means includes second electronic switch means, responsive to the channel select means, for switchably connecting a second control signal to the alternating current signal generator means and second channel circuit isolator means for electrically isolating the channel select means from the second electronic switch means.

Each of the first and second electronic switch means includes an alternating current actuated relay. The relay of the first electronic switch means includes a first coil, a first relay switch element electromagnetically responsive to the first coil and having first output means for providing a first control signal to the alternating current generator means, and a second relay switch element electromagnetically responsive to the first coil and interconnected with the third electrical winding. The relay of the second electronic switch means includes a second coil, a third relay switch element electromagnetically responsive to the second coil and having second output means for providing the second control signal to the alternating current generator means, and a fourth relay switch element electromagnetically responsive to the second coil and associated with the first coil and the second relay switch element so that current from the third electrical winding flows through the respective one, and only that one, of the first and second coils which is selected by the channel select means.

The channel select means includes first input means for connecting the second electrical winding to the channel select means. The channel select means further includes second input means for receiving an alternating current signal generated by said alternating current signal generator means, third input means for receiving a first channel select signal from the workpiece engaging means, and fourth input means for receiving a second channel select signal from the workpiece engaging means. The channel select means further includes workpiece signal output means associated with the second input means for transferring the alternating current signal from the alternating current generator means to the workpiece engaging means. Additionally, the channel select means includes coupling means for connecting the first input means and the third input means to the first channel circuit means and for connecting the first input means and the fourth input means to the second channel circuit means.

Therefore, from the foregoing it is a general object of the present invention to provide a novel and improved control unit for an electrosurgical generator apparatus. Other and further objects, features and advantages of the present invention will be readily apparent to those skilled in the art when the following description of the preferred embodiments is read in conjunction with the accompanying drawings.

DETAILED DESCRIPTION OF PREFERRED EMBODIMENTS OF THE INVENTION

Figure 1:
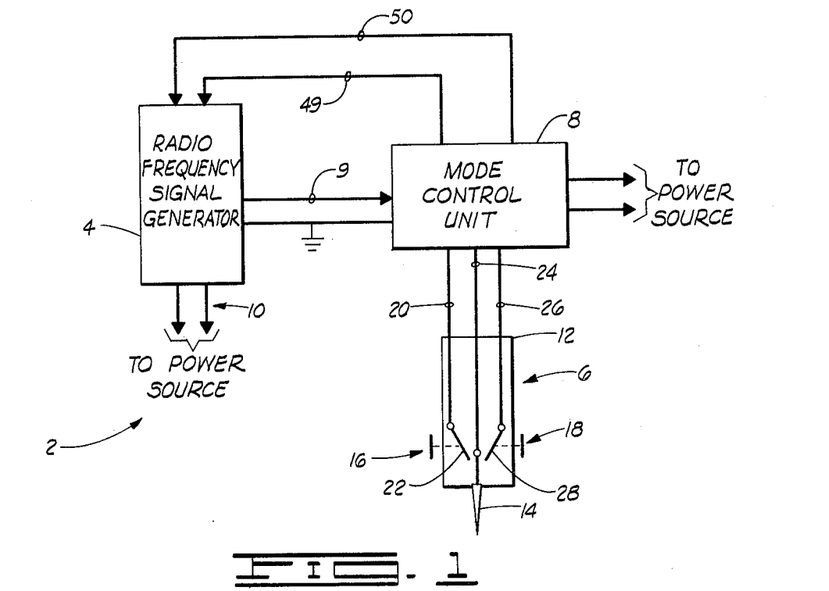
FIG. 1 is a schematic block diagram of an electrosurgical generator apparatus including a control unit constructed in accordance with the present invention.

With reference now to the drawings and in particular to FIG. 1, an apparatus constructed in accordance with the present invention will be described. In FIG. 1 an electronic surgical instrument 2 is schematically shown to include an alternating current signal generator means 4 (specifically shown as a radio frequency signal generator), a workpiece engaging means, such as a probe 6, and a control unit 8.

The alternating current signal generator means 4 is any suitable type of apparatus for generating an alternating current signal which can be surgically used to cut, coagulate, or otherwise affect tissue, such as human tissue. A preferred embodiment of the generator means is an electrosurgical generator identified by the name CSV Bovie which produces surgically usable alternating current signals at radio frequency with either sinusoidal or intermittent, exponentially decaying sinusoidal wave forms. These alternating current signals are provided to the control unit 8 as represented in FIG. 1 by the arrow labeled with reference numeral 9. There is also a system ground potential provided to the control 8 as symbolically shown in FIG. 1. As shown in FIG. 1, the alternating current signal generator means 4 includes a power cord 10 for connecting the generator 4 to an appropriate power supply, such as a nominal 110-volt AC outlet.

The probe 6 is a hand-held device including a housing 12 and an elongated member 14 extending therefrom. The probe 6 functions as a workpiece engaging means whereby the elongated member 14 engages the workpiece, such as the tissue to be cut or coagulated, to apply the radio frequency output from the alternating current signal generator means 4 thereto. FIG. 1 indicates that the housing 12 includes a first finger-actuated switch means 16 and a second finger-actuated switch means 18.

The probe 6 may be of any suitable type as is known in the art.

The first finger-actuated switch means 16 is connected by means of an electrical conductor 20 to the control unit 8 and includes a switch element 22 which may be manipulated into contact with an electrical conductor 24 conveying the output from the alternating current signal generator means 4 to the elongated member 14 of the probe 6. Similarly, the second finger-actuated switch means 18 is connected to the control means 8 by an electrical conductor 26 and includes a switch element 28 which may be manipulated into electrical contact with the conductor 24 coupling the generator means 4 output to the elongated member 14.

When the first finger-actuated switch means 16 is manipulated to couple the electrical conductor 20 to the conductor 24, a first channel select signal is provided to the control unit 8. When the second finger-actuated switch means 18 is manipulated to couple the electrical conductor 26 to the conductor 24, a second channel select signal is provided to the control unit 8. It is by means of the actuation of either the first or second finger-actuated switch means that the process by which the appropriate output wave form (e.g., sinusoidal or intermittent, exponentially decaying sinusoidal) from the alternating current signal generator means is commenced.

Figure 2:
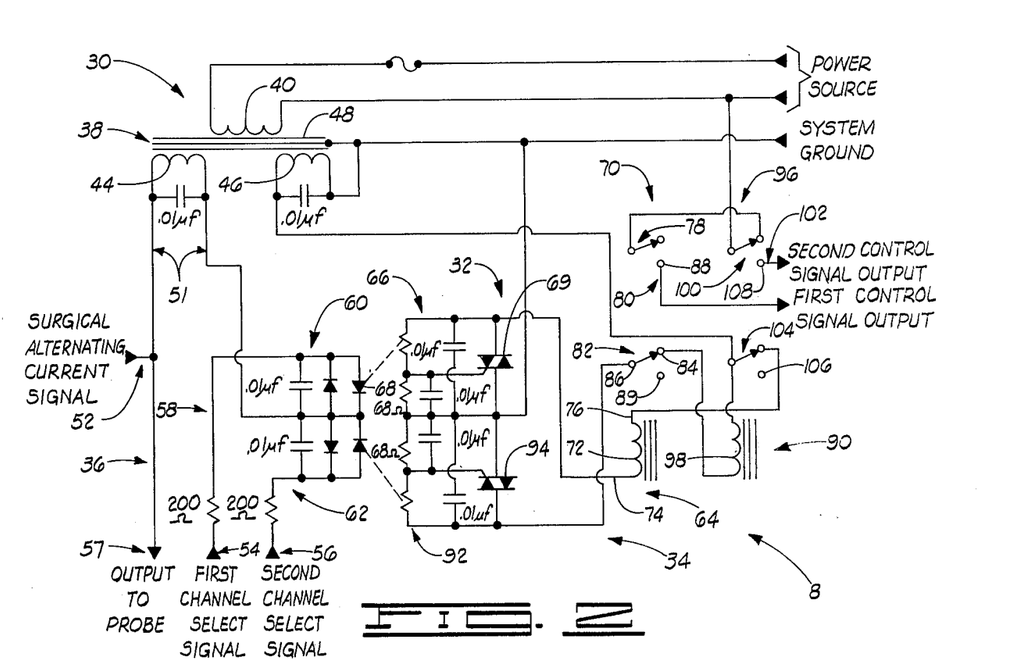
FIG. 2 is a schematic circuit diagram of a first preferred embodiment of the control unit of the present invention.

The details of the control unit 8 preferred embodiments by which the process for selecting the particular wave form is performed once either the first or second finger-actuated switch means is manipulated will be described with reference to FIGS. 2–4. FIG. 2 discloses a schematic circuit diagram of a first preferred embodiment of the control unit 8. This figure indicates that the control unit 8 includes power input means 30, first channel circuit means 32, second channel circuit means 34, and channel select means 36.

The power input means 30 includes a transformer 38 having a first electrical winding 40 with an input means for connecting it to a source of alternating current. This source of alternating current may either be obtained from the alternating current generating means 4 or an independent source, such as a nominal 110-volt AC power outlet. The power input means 30 further includes both a second electrical winding 44 associated with the channel select means 36 and a third electrical winding 46 associated with the first channel circuit means 32 and the second channel circuit means 34. To inductively couple the first electrical winding 40 with the second and third electrical windings 44 and 46, the power input means 30 further includes a core means 48 made of a suitable material as is known in the art.

The first electrical winding 40 is designated the primary winding of the transformer 38 and may be of the type which is energized by a nominal 110-volt AC, 60 hertz output, such as an ordinary wall socket outlet. Alternatively, the winding 40 may be energized by a lower voltage source, such as a transformer winding having a nominal 10-volt output which is located in the CSV Bovie electrosurgical generator preferably constituting the alternating current signal generating means 4. Other suitable sources of energization may also be used.

The second electrical winding 44 is a first secondary winding of the transformer 38 and is preferably constructed to withstand 8000 $V_{rms}$ to the other windings and core for one minute. The nominal operating voltage level for this winding is 4000 $V_{rms}$ as applied by the alternating current signal generator means 4. This winding operates in a two megahertz radio frequency circuit when used with the CSV Bovie electrosurgical generator. For safety purposes and for minimizing undue flow of reactive current to ground, the second electrical winding 44 should have a low capacitance to the system ground and should not short to the first electrical winding 40 if the insulation of the second electrical winding 44 fails and if the core means is at system ground.

The third electrical winding 46 is a second secondary winding and the regulation of the voltage output thereby is unimportant, as is the regulation of the voltage output by the second electrical winding 44. The capacitance to ground of the third electrical winding 46 is unimportant, and if the insulation surrounding the third winding 46 fails, the winding 46 should not short to the first electrical winding 40 assuming the core means 48 is at system ground.

As shown in FIG. 2, it is desirable that the core means 48 be connected to the system ground potential. This is achieved by connecting the core means 48 to the ground of the alternating current signal generator means 4 as symbolically shown in FIG. 1.

Associated with the second electrical winding 44 of the power input means is the channel select means 36. The channel select means 36 functions to selectively actuate either the first channel circuit means 32 or the second channel circuit means 34 so that when the first channel circuit means 32 is actuated, in response to having the appropriate finger-actuated switch means of the probe 6 manipulated, a first control signal is provided to the alternating current signal generator means 4 to activate the generation thereby of a first alternating current signal surgically usable by the workpiece engaging means. This first control signal is represented in FIG. 1 by the arrow labeled with reference numeral 49. For example, when the first finger-actuated switch means 16 is manipulated, the first channel circuit means 32 provides the first control signal 49 which causes the CSV Bovie electrosurgical generator to generate a continuous sinusoidal radio frequency signal and to send it as alternating current signal 9 to the control unit 8 so that it may be used to cut the tissue engaged by the elongated member 14 of the workpiece engaging means. Similarly, the channel select means 36 functions to actuate the second channel circuit means 34 in response to the appropriate finger-actuated switch of the probe 6 being actuated whereby a second control signal is provided to the alternating current signal generator means 4 to activate the generation thereby of a second alternating current signal surgically usable by the workpiece engaging means. This second control signal is represented in FIG. 1 by the arrow labeled with reference numeral 50. For example, when the second finger-actuated switch means 18 is manipulated so that the second channel select signal is provided to the control unit 18, the channel select means 36 actuates the second channel circuit means 34 to provide the second control signal 50 to the CSV Bovie generator to output the intermittent, exponentially decaying sinusoidal radio frequency signal as the signal 9 to the elongated member 14 of the workpiece engaging means via the control unit 8.

FIG. 2 indicates that the channel select means 36 includes first input means, such as electrical conductors 51, for connecting the second electrical winding 44 of the transformer 38 in the power input means 30 to the channel select means 36. The channel select means further includes second input means 52 for receiving the surgically usable alternating current output signal 9 generated by the alternating current signal generator means 4. A third input means 54 and a fourth input means 56 are also included within the channel select means 36 for respectively receiving a first channel select signal and a second channel select signal from the workpiece engaging means. Furthermore, the channel select means includes a workpiece signal output means 57 associated with the second input means 52 for transferring the alternating current output signal from the alternating current signal generating means 4 to the workpiece engaging means. There is also a coupling means 58 for connecting the first input means 51 and the third input means 54 to the first channel circuit means 32 and for connecting the first input means 51 and the fourth input means 56 to the second channel circuit means 34. As will be noted from FIG. 2, each of the input and output means includes appropriate electrical conductors and terminal means for receiving the respective electrical conductors from the elements with which the respective input and output means connect.

FIG. 2 discloses that the coupling means 58 of the preferred embodiment shown therein includes a first resistor/capacitor/diode (RCD) circuit 60 and a second resistor/capacitor/diode (RCD) circuit 62. FIG. 2 discloses that the diode of the first resistor/capacitor/diode circuit 60 is connected across the input of the first channel circuit means 32, and the diode of the second resistor/capacitor/diode circuit 62 is connected across the input of the second channel circuit means 34. Thus, it is apparent that when the conductors 20, 26 and 24 of the probe 6 are connected to the input means 54 and 56 and the output means 57, respectively, of the channel select means 36 and the first finger-actuated switch means 16 is manipulated to close the switch element 22, a current which is induced in the second electrical winding 44 is provided to the input of the first channel circuit means 32. Similarly, when the second finger-actuated switch means 18 of the probe 6 is closed, the current induced in the second electrical winding 44 is provided to the input of the second channel circuit means 34.

The first channel circuit means 32 functions to provide a first control signal to the alternating current signal generator means 4 whereby the first control signal causes the generator means to output a predetermined alternating current signal for transmission to the elongated member 14 of the probe 6. As previously mentioned, this first control signal is referenced in FIG. 1 by the numeral 49. The first channel circuit means 32 broadly includes a first electronic switch means 64, responsive to the channel selector means 36, for switchably connecting the first control signal to the alternating current signal generator means 4. The first channel circuit means 32 also includes first channel isolator means 66 for electrically isolating the channel select means 36 from the first electronic switch means 64. The first channel circuit isolator means 66 is shown in FIG. 2 to particularly include a photo-resistor optical isolator of the type known in the art. A photo diode 68 within the optical isolator 66 provides the inputs to which the coupling means of the channel select means 36 are connected. Specifically, FIG. 2 shows that the anode of the photo diode 68 is connected to the cathode of the diode of the first RCD means 60 and the cathode of the photo diode 68 is connected to the anode of the diode of the first RCD means 60 so that when the first finger-actuated switch means 16 is closed, the alternating current from the second electrical winding 44 actuates the photoresistor isolator means 66. This actuation of the photo diode 68 causes the first electronic switch means 64 to provide the first control signal to the alternating current signal generator means 4 as will be fully described hereinafter.

The first electronic switch means 64 shown in FIG. 2 includes a triac 69 which is switched into its conducting mode when the photo diode 68 is actuated by the channel select means 36. In addition to including the triac 69, the first electronic switch means includes a first relay 70. The first relay 70 includes a coil 72 having a first end 74 switchably associated, via the triac 69, with the first channel circuit isolator means 66 and also having a second end 76 associated with the third electrical winding 46 of the power input means. The relay 70 further includes a first relay switch element 78, electromagnetically responsive to the coil 72, and having output means 80 for providing the first control signal to the alternating current generator means 4. The relay further includes a second relay switch element 82, also electromagnetically responsive to the coil 72, having first terminal means 84 associated with the third electrical winding 46 and second terminal means 86 associated with the second channel circuit means 34.

It will be noted that when the triac 69 becomes conducting, an alternating current induced in the third electrical winding 46 will flow through the coil 72 of the first relay 70, thereby causing the first relay switch element 78 and the second relay switch element 82 to be moved from their positions shown in FIG. 2 downward adjacent lower terminals 88 and 89 shown therein. Such movement of the relay switch element 78 causes the first control signal 49 to be provided through the output means 80 to the alternating current signal generator means 4.

The second channel circuit means 34 provides a second control signal to the alternating current signal generator means 4 when the second finger-actuated switch means 18 of the probe 6 is appropriately manipulated. As previously mentioned, the second control signal is identified in FIG. 1 by the reference numeral 50. The second channel circuit means 34 is constructed similarly to the first channel circuit means 32 as shown in FIG. 2. In particular, the second channel circuit means includes second electronic switch means 90, responsive to the channel select means 36, for switchably connecting the second control signal to the alternating current signal generator means 4. The second channel circuit means 34 also includes second channel circuit isolator means 92 for electrically isolating the channel select means 36 from the second electronic switch means 90. As with the first channel circuit isolator means 66, the second channel circuit isolator means 92 includes a photo-resistor optical isolator for the preferred embodiment shown in FIG. 2. However, it is to be noted that either or both of the photo-resistor optical isolator means 66 or 92 may be replaced by any other suitable means for electrically isolating the channel select means circuit 36 from the respective electronic switch means circuits. As with the first channel circuit means 32, the second electronic switch means 90 includes a triac 94 which is switched into its conducting mode in response to the actuation by the channel selector means 36 of the second isolator means 92. Connected to the triac 94 is a second relay 96 which also forms a part of the second electronic switch means 90.

The second relay 96 includes a second coil 98 (through which the first terminal means 84 is associated with the winding 46 for the FIG. 2 embodiment), a third relay switch element 100 which is electromagnetically responsive to the second coil and has second output means 102 for providing the second control signal to the alternating current generator means 4, and a fourth relay switch element 104 which is electromagnetically responsive to the second coil 98 and is associated with the first coil 72 and the second relay switch element 82 so that current from the third electrical winding 46 flows through the respective one, and only that one, of the first coil 72 or second coil 98 which is selected by the channel select means 36. That is, when the first finger-actuated switch means 16 is manipulated, the current flows through the first coil 72 which, as previously mentioned, causes the second relay switch element 82 to move to its lower position thereby disconnecting the second coil 98 from a current conducting path. Likewise, when the second finger-actuated switch means 18 is appropriately manipulated, current flows through the second coil 98 thereby causing the fourth relay switch element 104 to move to its lower (as viewed in FIG. 2) position 106 and remove the first coil 72 from a current conducting path. When current flows through the second coil 98, the third relay switch element 100 is also moved to its downward position 108 as viewed in FIG. 2 so that the second control signal is provided through the second output means 102 from the second channel circuit means 34 to the alternating current signal generating means 4. It is to be noted that both the first and second relays are alternating current actuated relays.

By means of the power input means 30 and the relays 70 and 96, the control unit 8 is effectively isolated from both the primary power supply and the control signal inputs of the alternating current signal generator means 4. Isolation is also provided by means of the optical isolators 66 and 92. Furthermore, it will be noted that there are no internal oscillators within the control unit 8 which might cause electromagnetic interference with the operation of the circuits therein.

Figure 3:
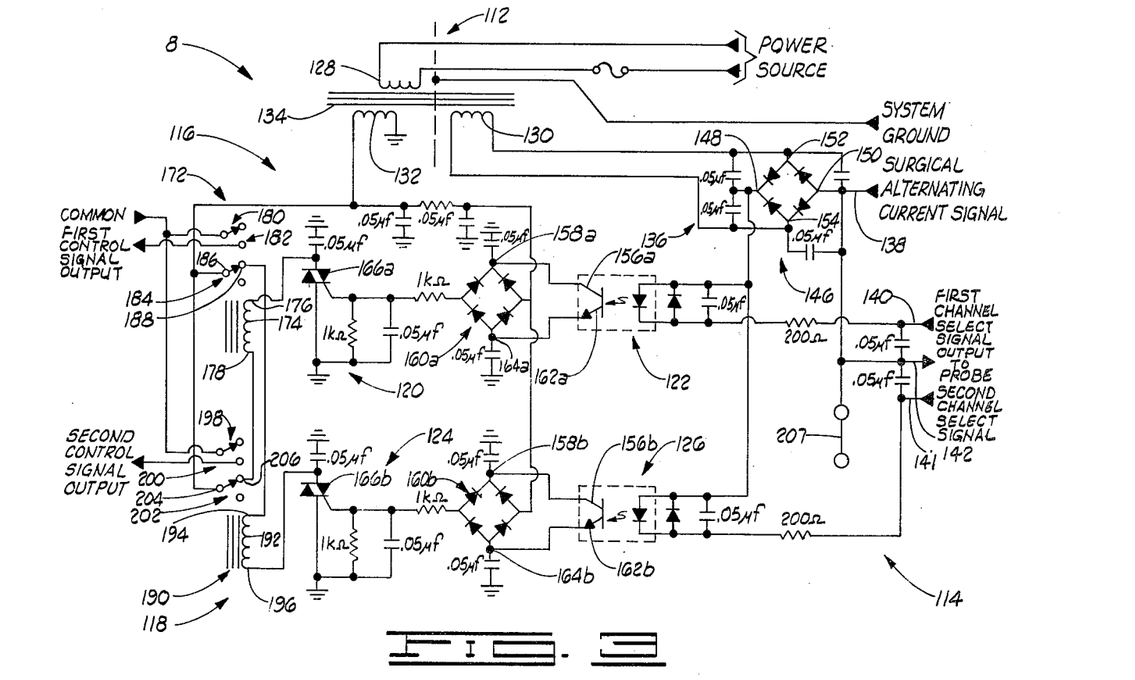
FIG. 3 is a schematic circuit diagram of a second preferred embodiment of the control unit of the present invention.

With reference to FIG. 3, a schematic circuit diagram of a second preferred embodiment of the present invention will be described. The preferred embodiment shown in FIG. 3 includes, similarly to FIG. 2 embodiment, power input means 112, a channel select means 114, a first channel circuit means 116, and a second channel circuit means 118. As with the FIG. 2 embodiment, the first channel circuit means 116 includes a first electronic switch means 120 and a first channel circuit isolator means 122, and the second channel circuit means 118 includes a second electronic switch means 124 and a second channel circuit isolator means 126.

The power input means 112 includes a first electrical winding 128 having first and second ends. When the FIG. 3 embodiment is used with the CSV Bovie electrosurgical generator, the first and second ends of the first electrical winding are connected to respective terminals of the generator so that a nominal 10 volt alternating current power source signal is provided to the first electrical winding 128. The power input means 112 further includes a second electrical winding 130, a third electrical winding 132, and a core means 134 for inductively coupling the first electrical winding 128 with the second and third electrical windings 130 and 132. In the preferred embodiment, the core means 134 is connected to the ground of the CSV Bovie electrosurgical generator.

As with the embodiment shown in FIG. 2, the FIG. 3 embodiment of the channel select means 114 includes first input means 136 for connecting the second electrical winding 130 to the channel select means 114, second input means 138 for receiving a surgically usable alternating current signal generated by the alternating current signal generator means, third input means 140 for receiving a first channel select signal from the workpiece engaging means, and fourth input means 141 for receiving a second channel select signal from the workpiece engaging means. The channel select means 114 further includes workpiece signal output means 142 associated with the second input means 138 for transferring the alternating current signal to the workpiece engaging means. A coupling means for connecting the first input means 136 and the third input means 140 to the first channel circuit means 116 and for connecting the first input means 136 and the fourth input means 141 to the second channel circuit means 118 is included within the channel select means 114 of the FIG. 3 embodiment.

The coupling means particularly includes a full-wave rectifier circuit means 146 having diode means defining a common cathode junction 148, a common anode junction 150, a first anode-cathode junction 152 and a second anode-cathode junction 154. The coupling means further includes means for connecting a first end of the second electrical winding 130 to the first anode-cathode junction 152 and means for connecting a second end of the second electrical winding 130 to the second anode-cathode junction 154. The coupling means also includes means for connecting the first channel circuit means 116 to the common cathode junction 148 and means for connecting the second channel circuit means 118 to the common cathode junction 148. The coupling means also includes means for connecting the second input means 138 and the workpiece signal output means 142 to the common anode junction 150. The coupling means further includes means for connecting the first channel circuit means 116 to the third input means 140. Also, the coupling means includes means for connecting the second channel circuit means 118 to the fourth input means 141. In particular, the second input means 138, third input means 140, fourth input means 141 and workpiece signal output means 142 include appropriate respective terminals to which are connected respective electrical conductors for connecting the respective terminals of the alternating current signal generator means 4 and the workpiece engaging means 6 thereto.

The first and second channel circuit isolator means 122 and 126 include, in the FIG. 3 embodiment, photo-Darlington optical isolators, such as Clairex C17-D isolators. Other types of isolators, such as suitably constructed photo-resistor and photo-triac isolators, may be used.

As shown in FIG. 3, each transistor element of each of the isolator means has a collector 156a or b connected to a common cathode junction 158a or b of a respective full-wave rectifier bridge 160a or b. An emitter 162a or b of the transistor element in each respective isolator means is connected to a common anode junction 164a or b of the respective full-wave rectifier circuit 160a or b. Each of these rectifier circuits forms a part of a respective one of the first and second electronic switch means 120 and 124.

Also forming a part of each electronic switch means shown in FIG. 3 is a respective triac 166a or b having its gate input coupled to one of the two anode-cathode junctions of the respective rectifier bridge 160a or b.

Further included in the first electronic switch means 120 is a relay 172 which is switched into an alternating current conducting path by means of the triac 166a. More particularly, the relay 172 of the first electronic switch means 120 includes a first coil 174 having a first end 176 switchably associated, via the triac 166a, with the first channel circuit isolator means 122 and further having a second end 178. The first relay 172 further includes a first relay switch element 180, electromagnetically responsive to the first coil 174, having first output means 182 for providing the first control signal to the alternating current generator means 4. Also included within the first relay 172 is a second relay switch element 184, electromagnetically responsive to the first coil 174, having first pole means 186 connected to the third electrical winding 132 and having first terminal means 188.

The second electronic switch means 124 includes a second relay 190 with a coil 192 having a first end 194 connected to the first terminal means 188 of the second relay switch element 184 and having a second end 196 switchably associated, via the triac 166b, with the second channel circuit isolator means 126. The second electronic switch means 124 further includes a third relay switch element 198, electromagnetically responsive to the second coil 192, having second output means 200 for providing the second control signal to the alternating current generator means 4. The relay 190 of the second electronic switch means further includes a fourth relay switch element 202, electromagnetically responsive to the second coil 192, having second pole means 204 connected to the third electrical winding 132 and having second terminal means 206 connected to the second end 178 of the first coil 174.

FIG. 3 also discloses that active jacks 207 may be included within the control unit 8. These jacks are operated by foot control as is known in the art. It is to be noted that similar jacks can be included in the embodiment shown in FIG. 2.

Operationally, the FIG. 3 embodiment functions so that when the third input means 140 is connected to the workpiece signal output means 6 and the first finger-actuated switch 16 is appropriately manipulated, a unidirectional current is applied through the rectifier bridge 146 to the photo-diode element within the first channel circuit isolator means 122. This current causes the transistor element in the isolator means 122 to become conductive thereby permitting the diodes within the rectifier bridge 160a to also become conductive and provide a current to the gate input of the triac 166a. This gate input current switches the triac 166a into its conductive state whereby an alternating current flows through the coil 174 of the first relay 172. This alternating current in the first coil 174 actuates the first and second relay switch elements 180 and 184 in a similar manner to that described with reference to FIG. 2. The switching of the first relay switch element 180 causes the first control signal to be provided to the alternating current signal generator means 4. A similar operation occurs when the second finger-actuated switch means 18 is appropriately manipulated so that a current is caused to flow through the second coil 192 of the second relay 190 whereby the third and fourth relay switch elements 198 and 202 are moved to provide the second control signal to the alternating current signal generator means 4. In response to either the first control signal or the second control signal, the alternating current signal generator 4 puts out the appropriate predetermined alternating current signal which is surgically usable at the elongated member of the probe 6.

It is to be understood from the preceding description and an analysis of the drawings that in the operation of the present invention when one of the relays (e.g., relay 172 in the FIG. 3 embodiment) is actuated, the other of the relays (e.g., relay 190 in the FIG. 3 embodiment) is locked-out so that no current can flow through its respective coil regardless of the status of the finger-actuated switch means associated with the locked-out relay. Therefore, only one control signal can be provided to the signal generator means at any one time.

Figure 4:
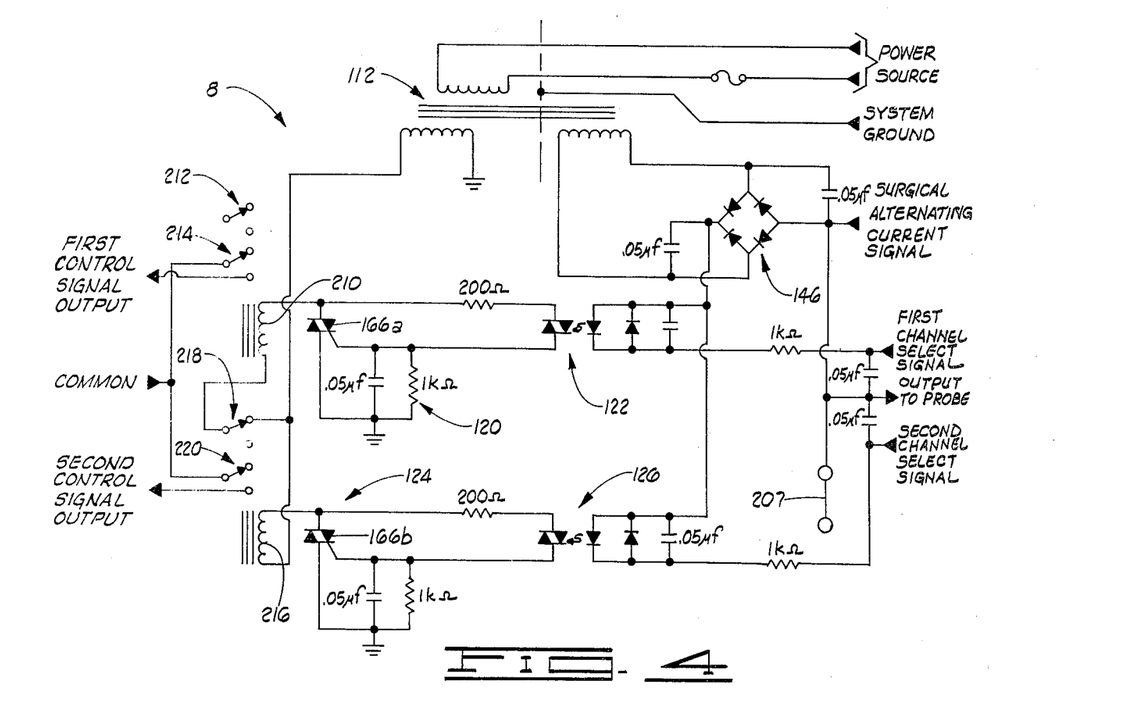
FIG. 4 is a schematic circuit diagram of a third preferred embodiment of the control unit of the present invention.

With reference to FIG. 4, a third preferred embodiment of the control unit 8 of the present invention will be described. As will be noted, the FIG. 4 embodiment is constructed somewhat similarly to the embodiments shown in FIGS. 2 and 3 as indicated by like numerals in FIG. 4 representing the same or similar elements as those shown in FIG. 3. One difference, however, is that the isolator means within each channel circuit means is disclosed to be a photo-triac optical isolator means. It is to be noted, though, that any suitable isolator means may be used.

A further difference is in the interconnection of the first and second relays. In the FIG. 4 embodiment, the first relay includes a first coil 210, a first relay switch element 214 and a second relay switch element 212. The second relay switch element 212 is disconnected from the circuit, whereas the first relay switch element 214 is connected so that when the first coil 210 is energized, the first control signal is provided to the alternating current signal generator means 4. The second relay includes a second coil 216, a third relay switch element 220, and a fourth relay switch element 218. The fourth relay switch element 218 is interconnected with the first coil 210 so that when the second coil 216 is energized, the first coil 210 is removed from a current conducting path. The third relay switch element 220 is connected so that when the second coil 216 is energized, a second control signal is provided to the alternating current signal generator means 4.

Operation of the FIG. 4 embodiment is substantially similar to the operation of the embodiment shown in FIGS. 2–3.

Althrough FIGS. 2–4 further disclose various components and component values for constructing the preferred embodiments disclosed therein, these are not to be taken as limiting the types of elements or their values which can be used to construct the present invention.

Thus, from an analysis of the drawings and the preceding description thereof, it will be noted that the embodiments of the present invention provide a control unit which isolates the primary power supply from each of two electrically isolated circuits within the control unit and isolates the control signals provided to the alternating current signal generator means from these same circuits. The isolation in the control circuits is achieved through the use of alternating current actuated relays which are responsive to a respective one of two channel select signals provided by a hand-held probe. Therefore, the present invention is well adapted to carry out the objects and attain the ends and advantages mentioned above as well as those inherent therein.

While preferred embodiments of the invention have been described for the purpose of this disclosure, numerous changes in the construction and arrangement of parts can be made by those skilled in the art, which changes are encompassed within the spirit of this invention as defined by the appended claims.

What is claimed is:

1. An apparatus for controlling an electronic surgical instrument which includes an alternating current signal generator means and a workpiece engaging means, said apparatus comprising:
    first channel circuit means for providing a first control signal to said alternating current signal generator means;
    second channel circuit means for providing a second control signal to said alternating current signal generator means;
    means for providing said first channel circuit means and said second channel circuit means with an alternating current to; and
    channel select means for selectably actuating either said first channel circuit means or said second channel circuit means so that when said first channel circuit means is actuated, the first control signal is provided to said alternating current signal generator means to activate the generation thereby of a first alternating current signal surgically usable by said workpiece engaging means and so that when said second channel circuit means is actuated, the second control signal is provided to said alternating current signal generator means to activate the generation thereby of a second alterating current signal surgically usable by said workpiece engaging means.

2. An apparatus as recited in claim 1, wherein said first channel circuit means includes:
    first electronic switch means, responsive to said channel select means, for switchably connecting the first control signal to said alternating current signal generator means; and
    first channel circuit isolator means for electrically isolating said channel select means from said first electronic switch means.

3. An apparatus as recited in claim 2, wherein said first electronic switch means includes an alternating current actuated relay.

4. An apparatus as recited in claim 2, wherein said second channel circuit means includes:
    second electronic switch means, responsive to said channel select means, for switchably connecting the second control signal to said alternating current signal generator means; and
    second channel circuit isolator means for electrically isolating said channel select means from said second electronic switch means.

5. An apparatus as recited in claim 4, wherein:
    said first electronic switch means includes a first alternating current actuated relay; and
    said second electronic switch means includes a second alternating current actuated relay.

6. An apparatus for controlling an electronic surgical instrument which includes an alternating current signal generator means and a workpiece engaging means, said apparatus comprising:
    first channel circuit means for providing a first control signal to said alternating current signal generator means;

second channel circuit means for providing a second control signal to said alternating current signal generator means;

means for energizing said first channel circuit means and said second channel circuit means with an alternating current, said means for energizing including:

a first electrical winding having an input means for connecting said first electrical winding to a source of alternating current;

a second electrical winding;

a third electrical winding associated with said first channel circuit means and said second channel circuit means; and core means for inductively coupling said first electrical winding with said second and third electrical windings; and channel select means, associated with said second electrical winding, for selectably actuating either said first channel circuit means or said second channel circuit means so that when said first channel circuit means is actuated, the first control signal is provided to said alternating current signal generator means to activate the generation thereby of a first alternating current signal surgically usable by said workpiece engaging means and so that when said second channel circuit means is actuated, the second control signal is provided to said alternating current signal generator means to activate the generation thereby of a second alternating current signal surgically usable by said workpiece engaging means.

7. An apparatus as recited in claim 6, wherein said core means is connected to a system ground potential.

8. An apparatus as recited in claim 6, wherein said channel select means includes:

first input means for connecting said second electrical winding to said channel select means;

second input means for receiving an alternating current signal generated by said alternating current signal generator means;

third input means for receiving a first channel select signal from said workpiece engaging means;

fourth input means for receiving a second channel select signal from said workpiece engaging means;

workpiece signal output means associated with said second input means for transferring the alternating current signal to said workpiece engaging means; and coupling means for connecting said first input means and said third input means to said first channel circuit means and for connecting said first input means and said fourth input means to said second channel circuit means.

9. An apparatus as recited in claim 6, wherein said first channel circuit means includes:

first electronic switch means, responsive to said channel select means, for switchably connecting the first control signal to said alternating current signal generator means; and first channel circuit isolator means for electrically isolating said channel select means from said first electronic switch means.

10. An apparatus as recited in claim 9, wherein said first electronic switch means includes a relay, comprising:

a coil having a first end switchably associated with said first channel circuit isolator means and a second end associated with said third electrical winding;

a first relay switch element, electromagnetically responsive to said coil, having output means for providing said first control signal to said alternating current generator means; and a second relay switch element, electromagnetically responsive to said coil, having first terminal means associated with said third electrical winding and second terminal means associated with said second channel circuit means.

11. An apparatus as recited in claim 9, wherein said second channel circuit means includes:

second electronic switch means, responsive to said channel select means, for switchably connecting the second control signal to said alternating current signal generator means; and second channel circuit isolator means for electrically isolating said channel select means from said second electronic switch means.

12. An apparatus as recited in claim 11, wherein:

said first electronic switch means includes:

a first coil;

a first relay switch element, electromagnetically responsive to said first coil, having first output means for providing said first control signal to said alternating current generator means; and a second relay switch element, electromagnetically responsive to said first coil, interconnected with said third electrical winding; and said second electronic switch means includes:

a second coil;

a third relay switch element, electromagnetically responsive to said second coil, having second output means for providing said second control signal to said alternating current generator means; and a fourth relay switch element, electromagnetically responsive to said second coil, associated with said first coil and said second relay switch element so that current from said third electrical winding flows through the respective one, and only that one, of said first and second coils which is selected by said channel select means.

13. An apparatus as recited in claim 12, wherein said channel select means includes:

first input means for connecting said second electrical winding to said channel select means;

second input means for receiving an alternating current signal generated by said alternating current signal generator means;

third input means for receiving a first channel select signal from said workpiece engaging means;

fourth input means for receiving a second channel select signal from said workpiece engaging means;

workpiece signal output means associated with said second input means for transferring the alternating current signal to said workpiece engaging means; and coupling means for connecting said first input means and said third input means to said first channel circuit isolator means and for connecting said first input means and said fourth input means to said second channel circuit isolator means.

14. An apparatus as recited in claim 11, wherein:

said first electronic switch means includes:

a first coil having a first end switchably associated with said first channel circuit isolator means and further having a second end;

a first relay switch element, electromagnetically responsive to said first coil, having first output means for providing said first control signal to said alternating current generator means; and a second relay switch element, electromagnetically responsive to said first coil, having first pole means connected to said third electrical winding and having first terminal means; and said second electronic switch means includes:

a second coil having a first end connected to said first terminal means of said second relay switch element and having a second end switchably associated with said second channel circuit isolator means;

a third relay switch element, electromagnetically responsive to said second coil, having second output means for providing said second control signal to said alternating current generator means; and a fourth relay switch element, electromagnetically responsive to said second coil, having second pole means connected to said third electrical winding and having second terminal means connected to the second end of said first coil.

15. An apparatus for controlling an electronic surgical instrument which includes an alternating current signal generator means and a workpiece engaging means, said apparatus comprising:

power input means, including:

a first electrical winding having an input means for connecting said first electrical winding directly to a source of alternating current;

a second electrical winding;

a third electrical winding; and core means for inductively coupling said first electrical winding with said second and third electrical windings;

channel circuit means for providing a control signal to said alternating current signal generator means, said channel circuit means including a relay having a coil associated with said third electrical winding; and channel select means, associated with said second electrical winding, for selectably actuating said channel circuit means to provide the control signal to said alternating current signal generator means.

16. An apparatus as recited in claim 15, wherein said core means is connected to a system ground potential.

17. An apparatus as recited in claim 15, wherein said second electrical winding has a low capacitance to ground.

18. An apparatus for controlling an electronic surgical instrument which includes an alternating current signal generator means and a workpiece engaging means, said apparatus comprising:

power input means, including:

a first electrical winding having an input means for connecting said first electrical winding to a source of alternating current;

a second electrical winding;

a third electrical winding; and core means for inductively coupling said first electrical winding with said second and third electrical windings;

channel circuit means for providing a control signal to said alternating current signal generator means, said channel circuit means including a relay having a coil associated with said third electrical winding; and channel select means, associated with said second electrical winding, for selectably actuating said channel circuit means to provide the control signal to said alternating current signal generator means, said channel select means including:

first input means for connecting said second electrical winding to said channel select means;

second input means for receiving an alternating current signal generated by said alternating current signal generator means;

third input means for receiving a channel select signal from said workpiece engaging means;

workpiece signal output means associated with said second input means for transferring the alternating current signal to said workpiece engaging means; and coupling means for connecting said first input means and said third input means to said channel circuit means.

19. An apparatus as recited in claim 18, wherein said coupling means includes:

a full wave rectifier circuit means having diode means defining a common cathode junction, a common anode junction, a first anode-cathode junction and a second anode-cathode junction;

means for connecting a first end of said second electrical winding to the first anode-cathode junction;

means for connecting a second end of said second electrical winding to the second anode-cathode junction;

means for connecting said channel circuit means to the common cathode junction and for connecting said channel circuit means to said third input means; and means for connecting said second input means and said workpiece signal output means to the common anode junction.

20. An apparatus as recited in claim 19, further comprising:

second channel circuit means for providing a second control signal to said alternating current signal generator means; and wherein said channel select means, in response to said workpiece engaging means, selectably actuates either said channel circuit means or said second channel circuit means so that when said channel circuit means is actuated, the control signal is provided to said alternating current signal generator means to activate the generation thereby of a first alternating current signal surgically usable by said workpiece engaging means and so that when said second channel circuit means is actuated, the second control signal is provided to said alternating current signal generator means to activate the generation thereby of a second alternating current signal surgically usable by said workpiece engaging means.

21. An apparatus as recited in claim 20, wherein:

said channel select means further includes fourth input means for receiving a second channel select signal from said workpiece engaging means; and said coupling means further includes means for connecting said second channel means to the common cathode junction and to said fourth input means.

* * * * *